United States Patent [19]

VandenBerg

[11] Patent Number: Plant 7,470

[45] Date of Patent: Mar. 12, 1991

[54] CHRYSANTHEMUM PLANT NAMED FORGE

[75] Inventor: Cornelis P. VandenBerg, Salinas, Calif.

[73] Assignee: Yoder Brothers, Inc., Barberton, Ohio

[21] Appl. No.: 416,668

[22] Filed: Oct. 2, 1989

[51] Int. Cl.[5] ..... A01H 5/00

[52] U.S. Cl. ..... Plt./74

[58] Field of Search ..... Plt./74, 78, 79

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Forge particularly characterized by its flat capitulum form; anemone capitulum type; yellow-orange ray floret color; diameter across face of capitulum of up to 55 mm at maturity with size of anemone cushion up to 32 mm when grown as a pinched spray pot mum; uniform eight week photoperiodic flowering response to short days; short plant height when grown as a pinched pot mum; and spreading and prolific branching pattern.

3 Drawing Sheets

The present invention comprises a new and distinct cultivar of Chrysanthemum, botanically known as *Dendranthema grandiflora*, and referred to by the cultivar name Forge.

Forge, identified as 85-912001, was originated from a cross made by Cornelis P. VandenBerg in a controlled breeding program in Salinas, Calif., in 1985.

The female parent of Forge was the cultivar identified as Rave, disclosed in U.S. Plan Pat. No. 5,738. The male parent of Forge was the cultivar identified as Vista, disclosed in U.S. Plant Pat. No. 5,353.

Forge was discovered and selected as one flowering plant within the progeny of the stated cross by Cornelis P. VandenBerg Nov. 18, 1985, in a controlled environment in Salinas, Calif.

The first act of asexual reproduction of Forge was accomplished when vegetative cuttings were taken from the initial selection in January of 1986 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Forge are firmly fixed and are retained through successive generations of asexual reproduction.

Forge has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Forge, which, in combination, distinguish this Chrysanthemum as a new and distinct cultivar:

1. Flat capitulum form.
2. Anemone capitulum type.
3. Yellow-orange ray floret color
4. Diameter across face of capitulum up to 55 mm at maturity, with size of anemone cushion up to 32 mm, when grown as a pinched spray pot mum.
5. Uniform eight week photoperiodic flowering response to short days.
6. Short plant height, requiring 7 to 14 long days after pinch prior to short days and 1 and 2 applications of 2500 ppm B-9 SP to attain a flowered plant height of 25 to 35 cm for year-round flowerings when grown as a pinched pot mum in a 15 cm pot.
7. Branching pattern is spreading and prolific.

The accompanying photographic drawings show typical inflorescence and leaf characteristics of Forge, with the colors being as nearly true as possible with illustrations of this type.

Sheet 1 is a color photograph of Forge grown as a pinched spray pot mum in a 15 cm pot.

Sheet 2 is a black and white photograph of three views of the inflorescence of Forge.

Sheet 3 is a black and white photograph showing the upper and under sides of the leaves of Forge at three stages of development (mature, intermediate and immature).

Of the commercial cultivars known to the inventor, the most similar in comparison to Forge is the male parent Vista. Reference is made to attached Chart A, which compares certain characteristics of Forge to the same characteristics of Vista.

Similar traits are copitulum form and type, branching pattern, and plant height. Forge has a deeper, more orange flower color than Vista, a slightly larger diameter of capitulum and a slower flowering response to short days than Vista. In addition, the spray formation of Vista is often clubby, while the spray formation of Forge is more open, with a much better display of the flowers.

In the following description, color references are made to The Royal Horticultural Society Colour Chart. The color values were determined on plant material grown as a pinched spray pot mum in Salinas, Calif. on Jun. 5, 1989.

Classification:

*botanical.*—Dendranthema grandiflora cv Forge.

*Commercial.*—*Anemone spray pot mum.*

INFLORESCENCE

A. Capitulum:

*Form.*—Flat.

*Type.*—Anemone.

*Diameter across face.*—Up to 55 mm at maturity.

*Diameter of anemone cushion.*—up to 32 mm.

B. Corolla of ray florets:

*Color (general tonality from a distance of three meters).*—Yellow-orange.

*Color (upper surface).*—14A to 14B.

*Color (under surface).*—10A to 10B.

*Shape.*—Flat, straight, oblong.

C. Corolla of disc florets (Anemone cushion):

*Color (mature).*—14B with overcast of 21B.

*Color (immature).*-14B with slight overcast of 144C.

D. Reproductive organs:

*Androecium.*—Present on disc florets only; no pollen.

*Gynoecium.*—Present on both ray and disc florets.

PLANT

A. General appearance:

*Height.*—Short; 25 to 35 cm as a pinched spray pot mum with 7 to 14 long days after pinch prior to short days and 1 to 2 applications of 2500 ppm B-9 SP when grown in a 15 cm pot.

*Branching pattern.*—Spreading and prolific.

B. Foliage:

*Color (upper surface).*—147A.

*Color (under surface).*—147B.

*Shape.*—Deeply lobed and serrated.

CHART A

COMPARISON OF FORGE AND VISTA

| CHARACTERISTIC | FORGE | VISTA |
|---|---|---|
| Ray Floret Color | Yellow-orange | Light bronze to golden yellow |
| Capitulum Form and Type | Flat anemone | Flat anemone |
| Branching Pattern | Spreading and prolific | Spreading and prolific |
| Diameter Across Face of Capitulum | Up to 55 mm | 35 to 50 mm |
| Plant Height | Short | Short |
| Controlled Flowering | 8 weeks | 7 weeks |

Comparisons Made of Plants Grown
As Pinched Spray Pot Mums
In Salinas, California

I claim:

1. A new and distinct Chrysanthemum plant named Forge, as described and illustrated.

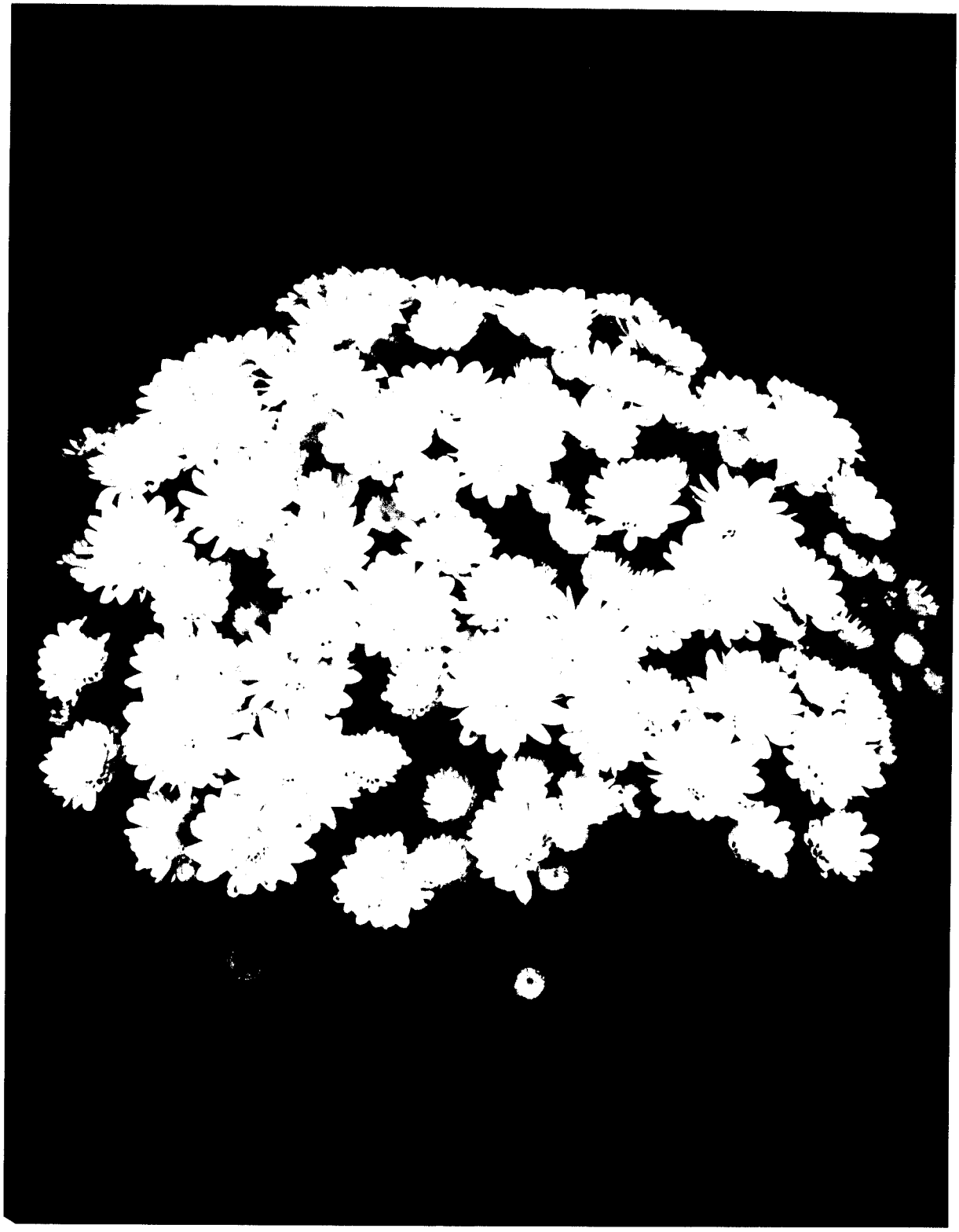

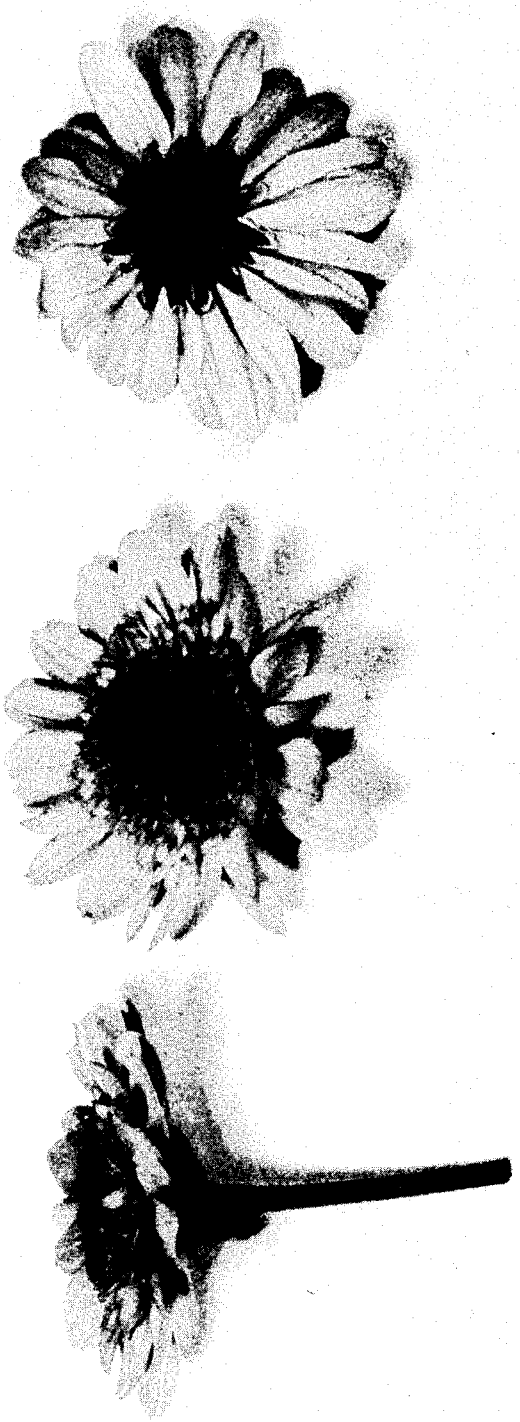

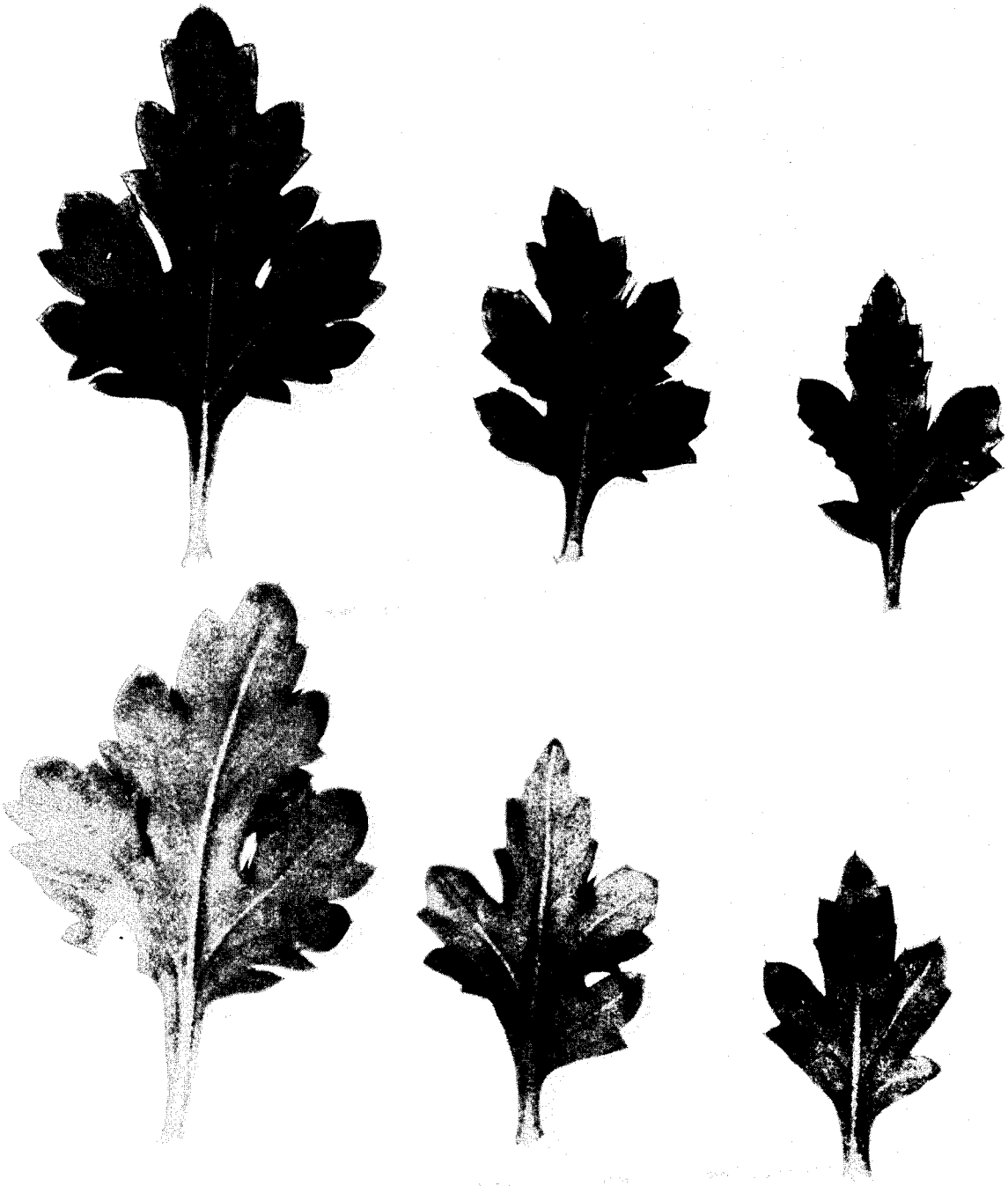

* * * * *